US008206744B2

(12) United States Patent
Soula et al.

(10) Patent No.: US 8,206,744 B2
(45) Date of Patent: Jun. 26, 2012

(54) BRANCHED POLYAMINO ACIDS FUNCTIONALIZED WITH HYDROPHOBIC GROUPS, AND APPLICATIONS THEREOF PARTICULARLY THERAPEUTIC APPLICATIONS

(75) Inventors: Rémi Soula, Lyons (FR); Gauthier Pouliquen, Lyons (FR); You-Ping Chan, Lyons (FR)

(73) Assignee: Flamel Technologies (FR)

( * ) Notice: Subject to any disclaimer, the term of this patent is extended or adjusted under 35 U.S.C. 154(b) by 878 days.

(21) Appl. No.: 11/658,875

(22) PCT Filed: Jul. 19, 2005

(86) PCT No.: PCT/FR2005/050594
§ 371 (c)(1),
(2), (4) Date: Jul. 22, 2009

(87) PCT Pub. No.: WO2006/021706
PCT Pub. Date: Mar. 2, 2006

(65) Prior Publication Data
US 2009/0305948 A1    Dec. 10, 2009

(30) Foreign Application Priority Data
Jul. 30, 2004    (FR) ..................... 04 08477

(51) Int. Cl.
*A61K 9/00*    (2006.01)
*A61K 47/42*    (2006.01)
*C08G 83/00*    (2006.01)

(52) U.S. Cl. ............... 424/486; 514/772.1; 525/54.1
(58) Field of Classification Search .............. None
See application file for complete search history.

(56) References Cited

U.S. PATENT DOCUMENTS

| | | | |
|---|---|---|---|
| 4,351,337 | A | 9/1982 | Sidman |
| 4,652,441 | A | 3/1987 | Okada et al. |
| 4,888,398 | A | 12/1989 | Bichon et al. |
| 5,449,513 | A | 9/1995 | Yokoyama et al. |
| 5,904,936 | A | 5/1999 | Huille et al. |
| 6,153,193 | A | 11/2000 | Kabanov et al. |
| 6,630,171 | B1 | 10/2003 | Huille et al. |
| 2002/0102217 | A1* | 8/2002 | Klaveness et al. ........ 424/9.52 |

FOREIGN PATENT DOCUMENTS

| | | |
|---|---|---|
| FR | 2 801 226 | 5/2001 |
| WO | WO-87/03891 | 7/1987 |
| WO | WO-8703891 | 7/1987 |
| WO | WO-99/61512 | 12/1999 |
| WO | WO-9961512 | 12/1999 |
| WO | WO-03/104303 | 12/2003 |
| WO | WO-03104303 | 12/2003 |
| WO | WO-2004/013206 | 2/2004 |
| WO | WO-2004013206 | 2/2004 |
| WO | WO-2004/060968 | 7/2004 |
| WO | WO-2004060968 | 7/2004 |

OTHER PUBLICATIONS

Akiyoshi et al., Self-Assembled Hydrogel Nanoparticle of Cholesterol-Bearing Pullulan as a Carrier of Protein Drugs: Complexation and Stabilization of Insulin, J. Controlled Release 54: 313-320 (1998).
Bodanszky, Principles of Peptide Synthesis, Springer Verlag, Berlin, (1984).
Fuller, A Procedure for the Facile Synthesis of Amino-Acid N-Carboxyanhydrides, Biopolymers 15: 1869-1871 (1976).
Tomida et al., Convenient Synthesis of High Molecular Weight Poly(Succinimide) by Acid-Catalysed Polycondensation of L-Aspartic Acid, Polymer 38: 4733-36 (1997).
Akiyoshi et al., "Self-Assembled Hydrogel Nanoparticle of Cholesterol-Bearing Pullulan as a Carrier of Protein Drugs: Complexation and Stabilization of Insulin," J. Controlled Release, 1998; 54:313-320.
Bodanszky, "Princliples of Peptide Synthesis," Springer Verlag, Berlin, 1984.
Fuller, "A Procedure for the Facile Synthesis of Amino-Acid N-Carboxyanhydrides," Biopolymers, 1976; 15:1869-1871.
Gupta et al., "Injectable Drug Development," Interpharm Press, Denver, CO, 1999; 401-421.
Kreuter, "Colloidal Drug Delivery Systems," Marcel Dekker, Inc., New York, NY, 1994; 66:219-342.

* cited by examiner

Primary Examiner — Jeffrey E Russel
(74) Attorney, Agent, or Firm — Patton Boggs LLP

(57) ABSTRACT

The invention concerns novel materials based on biodegradable branched polyaminoacids particularly useful for transporting active principle(s). The invention also concerns novel pharmaceutical, cosmetic, dietetic or phytosanitary compositions based on polyaminoacids. The invention aims at providing a novel polymeric material, capable of being used for transporting active principle(s) and enabling all the required relevant specifications to be optimally satisfied: biocompatibility, biodegradability, easy ability to be combined with a large number of active principles or to solubilize same, and to release the active principles in vivo. This is achieved by the present invention which firstly concerns branched polyaminoacids comprising aspartic acid units and or glutamic acid units, and which bear hydrophobic groups including 8 to 30 carbon atoms. The branched polyaminoacids are amphiphilic and are capable of being easily and economically transformed into particles for transporting active principles, the particles being themselves capable of forming stable aqueous colloidal suspensions.

15 Claims, 1 Drawing Sheet

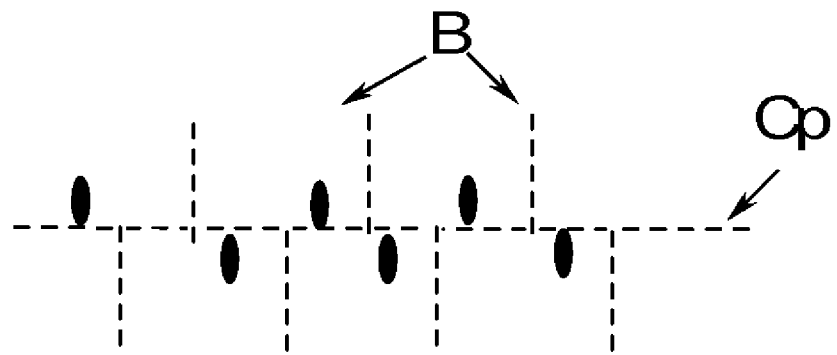
*(I)*
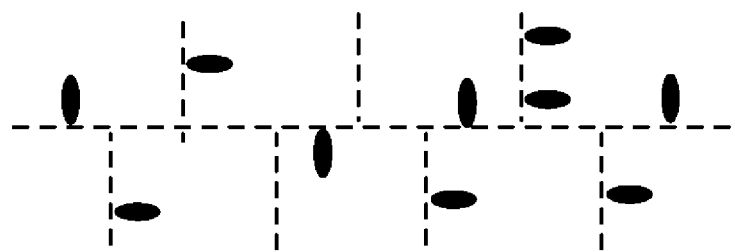
*(II)*
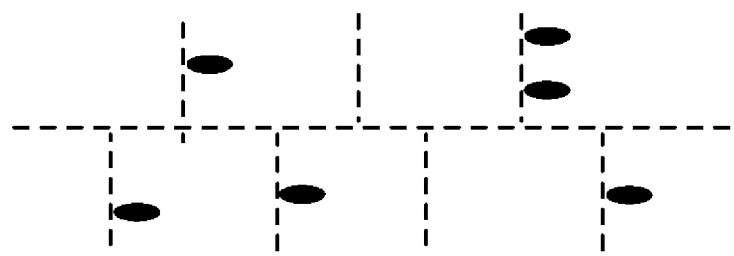
*(III)*

BRANCHED POLYAMINO ACIDS FUNCTIONALIZED WITH HYDROPHOBIC GROUPS, AND APPLICATIONS THEREOF PARTICULARLY THERAPEUTIC APPLICATIONS

CROSS-REFERENCES TO RELATED APPLICATIONS

This application claims priority to PCT/FR2005/050594, filed Jul. 19, 2005, which claims priority to FR 04 08477, filed Jul. 30, 2004. The contents of which are incorporated herein in their entirety.

The present invention relates to novel materials based on biodegradable polyamino acids that are useful especially for the vectorization of one or more active principles (AP).

The invention further relates to novel pharmaceutical, cosmetic, dietetic or phytosanitary compositions based on these polyamino acids. These compositions can be of the type allowing the vectorization of AP and preferably taking the form of emulsions, micelles, particles, gels, implants or films.

The AP in question are advantageously biologically active compounds which can be administered to an animal or human organism by the oral, parenteral, nasal, vaginal, ocular, subcutaneous, intravenous, intramuscular, intradermal, intraperitoneal, intracerebral, buccal or other route.

The AP to which the invention relates more particularly, but without implying a limitation, are proteins, glycoproteins, peptides, polysaccharides, lipopolysaccharides, oligonucleotides or polynucleotides, and organic molecules. However, they can also be cosmetic products or phytosanitary products such as herbicides, insecticides, fungicides, etc.

In the field of the vectorization of active principles, especially medicinal active principles, there is a need in many cases to:
  protect them from degradation (hydrolysis, precipitation at the site, enzymatic digestion, etc.) until they reach their site of action,
  and/or control their rate of release so as to maintain a therapeutic level over a defined period,
  and/or transport them (with protection) to the site of action.

For these purposes, several types of polymers have been studied and some are even available commercially. Examples which may be mentioned are polymers of the polylactic, polylactic-glycolic, polyoxyethylene-oxypropylene, polyamino acid or polysaccharide type. These polymers constitute starting materials for the manufacture of e.g. mass implants, microparticles, nanoparticles, vesicles, micelles or gels. In addition to the fact that these polymers have to be suitable for the manufacture of such systems, they must also be biocompatible, non-toxic, non-immunogenic and economic and they must be easy to eliminate from the body and/or biodegradable. On this last point, it is further essential that biodegradation in the organism generates non-toxic products.

Another very important point in the development of an associative polymer is its solubility in water. The possibility of solubilizing a large amount of polymer allows the polymer/active principle ratio to be adapted to the desired release profile.

Various patents, patent applications or scientific articles are referred to below in order to illustrate the prior art relating to polymers employed as starting materials for the preparation of AP vectorization systems.

U.S. Pat. No. 4,652,441 describes polylactide microcapsules encapsulating the hormone LH-RH. These microcapsules are produced by preparing a water-in-oil-in-water emulsion and comprise an aqueous inner layer containing the hormone, a substance (gelatin) for fixing the latter, an oily polylactide layer and an aqueous outer layer (polyvinyl alcohol). The AP can be released over a period of more than two weeks after subcutaneous injection.

U.S. Pat. No. 6,153,193 describes compositions based on amphiphilic poly(oxyethylene)-poly(oxypropylene) micelles for the vectorization of anticancer agents such as adriamycin.

Akiyoshi et al. (J. Controlled Release 1998, 54, 313-320) describe pullulans which are rendered hydrophobic by the grafting of cholesterol and form nanoparticles in water. These nanoparticles, which are capable of complexing reversibly with insulin, form stable colloidal suspensions.

U.S. Pat. No. 4,351,337 describes amphiphilic copolyamino acids based on leucine and glutamate which can be used in the form of implants or microparticles for the controlled release of active principles. The latter can be released over a very long period, depending on the rate of degradation of the polymer.

U.S. Pat. No. 4,888,398 describes polymers based on polyglutamate or polyaspartate, and optionally polyleucine, with pendent groups of the alkoxy-carbonylmethyl type randomly located along the polyamino acid chain. These polyamino acids, grafted with side groups, e.g. methoxycarbonylmethyl groups, can be used in the form of prolonged-release biodegradable implants containing an AP.

U.S. Pat. No. 5,904,936 describes nanoparticles obtained from a polyleucine-polyglutamate block polymer which are capable of forming stable colloidal suspensions and of associating spontaneously with biologically active proteins without denaturing them. The latter can then be released in vivo in a controlled manner over a long period.

U.S. Pat. No. 5,449,513 describes amphiphilic block copolymers comprising a polyoxyethylene block and a polyamino acid block, e.g. poly(beta-benzyl-L-aspartate). These polyoxyethylene-polybenzylaspartate polymers form micelles capable of encapsulating hydrophobic active molecules such as adriamycin or indomethacin.

Patent application WO-A-99/61512 describes polylysines and polyornithines functionalized with a hydrophobic group (palmitic acid joined to the polylysine or polyornithine) and a hydrophilic group (polyoxyethylene). In the presence of cholesterol, these polymers, e.g. polylysine grafted with polyoxyethylene and palmitoyl chains, form vesicles capable of encapsulating doxorubicin or DNA. These polymers based on polylysines are cationic in a physiological medium.

U.S. Pat. No. 6,630,171 in the name of the Applicant describes poly(sodium glutamate)-poly(methyl, ethyl, hexadecyl or dodecyl glutamate) block or random polymers capable of forming stable colloidal suspensions and of associating spontaneously with biologically active proteins without denaturing them. The latter can then be released in vivo in a controlled manner over a long period. These amphiphilic linear copolyamino acids are modified by the presence of a hydrophobic alkyl side chain. These alkyl groups are covalently grafted onto the polymer via an ester group. These polymers are anionic in a physiological medium.

In the same field, the Applicant has described polyglutamate-based polymers with related designs in several patent applications.

Patent application WO-A-03/104303 describes anionic polyamino acids functionalized with alpha-tocopherol. Patent application WO-A-04/013206 describes anionic polyamino acids containing hydrophobic groups and characterized in that these groups are joined to the polymer via a spacer containing two amide groups, and more precisely via a spacer of the lysine or ornithine type.

Unpublished patent application PCT/FR03/03458 describes polyamino acids functionalized with at least one oligoamino acid group based on leucine and/or isoleucine and/or valine and/or phenylalanine.

Patent application WO-A-87/03891 describes amphiphilic linear, branched or star-shaped polymers with at least two hydrophobic groups bonded only to their ends. Said patent application relates essentially to neutral hydrophilic polymers based on polyethylene glycol, as evidenced by all the Examples in said patent. Now, this type of polymer is not biodegradable, which constitutes a major disadvantage.

Thus, although there are a very large number of technical solutions in the prior art which have been developed and proposed for the vectorization of medicinal active principles, it is difficult to respond to all the demands and the situation remains unsatisfactory. More specifically, it has been possible to identify an unsatisfied need for a biodegradable material for producing particles for the vectorization of active principles, which material should be capable of forming an aqueous suspension of vectorization nanoparticles or microparticles suitable for associating reversibly with active principles, and in which one of the desired improvements would be to have the highest possible polymer/active principle ratio.

In this context, one of the essential objects of the present invention is to provide novel amphiphilic branched polyamino acids anionic at animal physiological pH (e.g. in the order of 7.4) which represent an improvement relative to those described in U.S. Pat. No. 6,630,171, WO-A-03/104303, WO-A-04/013206 and PCT/FR03/03458 (unpublished), especially in terms of the formulation of an active principle such as a therapeutic protein.

Another essential object of the present invention is that these polymers are capable of being used for the vectorization of AP and make it possible optimally to satisfy all the specifications of the specifications sheet, namely, in particular:
  capacity:
    easily and economically to form stable aqueous colloidal suspensions,
    easily to associate with numerous active principles,
    and to release these active principles in vivo,
  biocompatibility,
  biodegradability,
  stability to hydrolysis.

This and other objects are achieved by the present invention, which relates first and foremost to a polyamino acid comprising aspartic units and/or glutamic units, some of which carry one or more mutually identical or different hydrophobic groups (GH), characterized in that it comprises at least one type of polyamino acid main chain Cp containing aspartic units and/or glutamic units and having one or more mutually identical or different polyamino acid branches B containing aspartic units and/or glutamic units.

According to one particularly preferred characteristic of the branched polyamino acid according to the invention, the hydrophobic grafts are bonded to:
  (I) the main chain Cp only,
  (II) the main chain Cp and the branch(es) B,
  (III) or the branch(es) B only.

BRIEF DESCRIPTION OF THE DRAWINGS

FIG. 1 is an illustration of three preferred families (I), (II) and (III) of branched polyamino acids.

It is to the Applicant's credit to have developed an amphiphilic branched polyamino acid carrying mutually identical or different GH randomly distributed throughout the branched structure.

The polyamino acid in question can be a homopolymer (poly[Glu] or poly[Asp]) or copolymer (poly[Glu]-poly[Asp]).

The three preferred families (I), (II) and (III) of branched polyamino acid according to the invention are symbolically represented in FIG. 1 where the dotted lines ( - - - - - ) represent the polyamino acid main chains Cp or branches B and the filled ovals (●) represent the hydrophobic grafts.

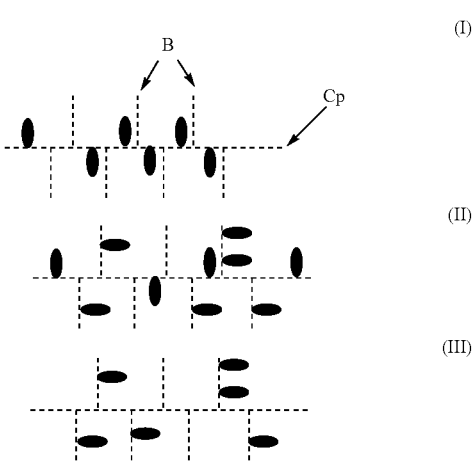

The structures of the families (I), (II) and (III) differ in the grafting positions of the hydrophobic groups:
  in structure (I) the grafts are randomly located on the chain Cp (or skeleton) only;
  in structure (II) the grafts are randomly located both on the chain Cp (or skeleton) and on the branches B;
  in structure (III) the grafts are randomly located on the branches B only.

To obtain the preferred families (I), (II) and (III), it is to the Applicant's credit to have had the idea of combining, in a totally judicious and advantageous manner, specific biodegradable branched polyamino acids (preferably homopolyamino acids) (e.g. polyAsp or polyGlu) with hydrophobic groups GH.

These novel amphiphilic branched polymers have proved particularly suitable for the vectorization of proteins.

As defined in the invention:
  the term "polyamino acid" covers on the one hand PAA containing a single type of "amino acid" unit (e.g. either Glu (glutamic or glutamate) units or Asp (aspartic or aspartate) units, or a copolyamino acid (containing a mixture of Glu and Asp amino acid units in a concatenation of random, gradient or block type), and on the other hand both oligoamino acids comprising from 2 to 20 "amino acid" units and polyamino acids comprising more than 20 "amino acid" units;
  the term "amino acid unit" relates to a monomeric or non-monomeric unit formed of a skeleton of a given amino acid, regardless of what the substituents might be, provided they do not modify the nature of the amino acid in question.

These polymers have surprising properties of fluidity, association and/or encapsulation with one or more active principles, compared with analogous products.

In addition, they are easily degraded in the presence of enzymes to non-toxic catabolites/metabolites (amino acids).

As defined in the invention and throughout the present disclosure, the terms "association" or "associate" employed to qualify the relationships between one or more active principles and the homopolyamino acids denote in particular that the active principle(s) is (are) bonded to the homopolyamino acid(s) especially by a weak bond, e.g. by ionic bonding and/or hydrophobic contact, and/or are encapsulated by the homopolyamino acid(s).

Advantageously, at least one of the hydrophobic groups GH is included in a hydrophobic graft comprising at least one spacer, making it possible to join the hydrophobic group GH to a chain of the polyamino acid (e.g. a polyamino acid main chain or skeleton). This spacer can comprise e.g. at least one direct covalent bond and/or at least one amide linkage and/or at least one ester linkage. For example, the spacer can be of the type belonging to the group comprising different "amino acid" units from the constituent monomeric unit of the polyamino acid, amino alcohol derivatives, diamine derivatives, diol derivatives and hydroxy acid derivatives.

The grafting of the GH onto the polyamino acid chain can proceed via the use of precursors of GH that are capable of bonding to the polyamino acid chain.

In practice and without implying a limitation, the precursors of GH are selected from the group comprising alcohols and amines, these compounds being easily functionalizable by those skilled in the art. The grafting of the GH is explained in greater detail below in the description of the process for obtaining the polyamino acids according to the invention.

According to one preferred characteristic, the hydrophobic group GH of the hydrophobic graft contains from 8 to 30 carbon atoms.

These hydrophobic groups GH are advantageously and judiciously selected from the group comprising:
- linear or branched C8 to C30 alkyls which can optionally contain at least one unit of unsaturation and/or at least one heteroatom,
- C8 to C30 alkylaryls or arylalkyls which can optionally contain at least one unit of unsaturation and/or at least one heteroatom, and
- C8 to C30 (poly)cyclics which can optionally contain at least one unit of unsaturation and/or at least one heteroatom.

According to one preferred characteristic of the invention, at least one hydrophobic graft, preferably the hydrophobic group(s) GH of said graft, has at least one anionic charge and/or one or more mutually identical or different ionizable groups, each of which is capable of giving rise to at least one anionic charge.

Advantageously, the anionic or anionizable character of all or some of the hydrophobic grafts is given by the GH. It follows that all or some of the hydrophobic groups GH of the hydrophobic grafts each have at least one anionic charge and/or at least one ionizable group capable of giving rise to at least one anionic charge.

Preferably, the ionizable group of GH capable of giving rise to at least one anionic charge is selected from the group comprising the carboxylic/carboxylate group, the sulfonic/sulfonate group, the sulfuric/sulfate group and the phosphoric/phosphate group.

If they are not ionized or ionizable, the hydrophobic groups GH can be derived e.g. from groups selected from the group comprising octanol, dodecanol, tetradecanol, hexadecanol, octadecanol, oleyl alcohol, tocopherol, cholesterol and lithocholic acid.

Preferably, the (homo)polyamino acids according to the present invention are homooligomers or homopolymers comprising alpha-L-glutamate and/or alpha-L-glutamic units or alpha-L-aspartate and/or alpha-L-aspartic units.

Very particularly preferably, the polyamino acids according to the invention are polyglutamates of general formulae (I), (II) and (III) below:

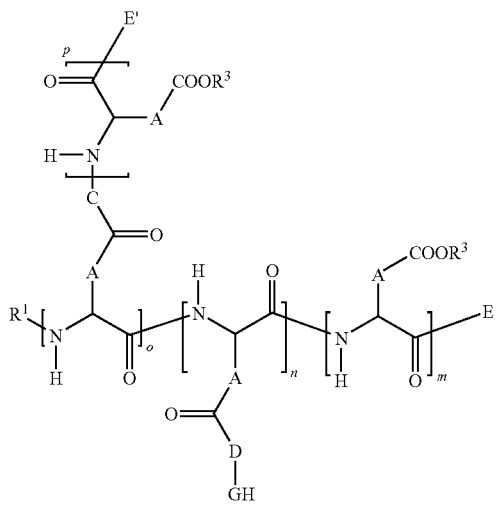

(I)

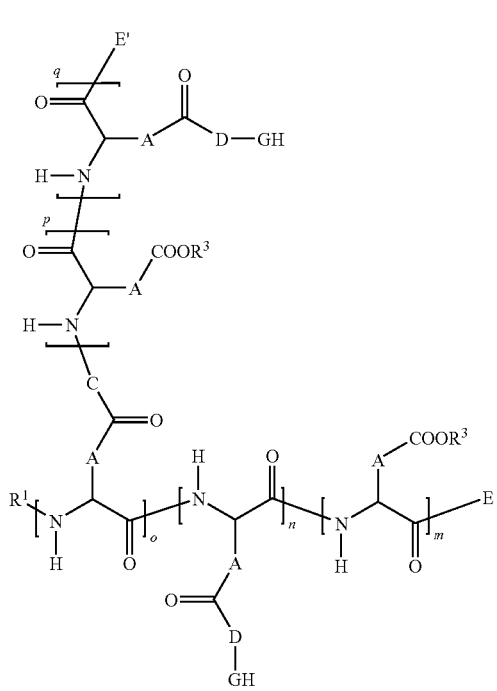

(II)

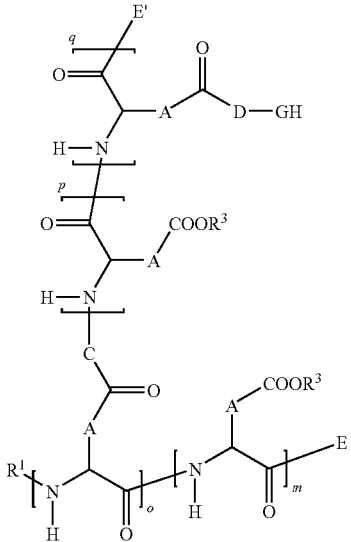

in which:
A independently is —CH$_2$— (aspartic unit) or —CH$_2$—CH$_2$— (glutamic unit);
R$^1$ is H, a linear C2 to C10 or branched C3 to C10 acyl group, or pyroglutamate;
E, E' independently are:
  OR$^3$, R$^3$ being as defined below,
  a group NHR$^2$, in which R$^2$ is H, a linear C2 to C10 or branched C3 to C10 alkyl, or benzyl, or
  a terminal amino acid unit which is bonded by the nitrogen and whose acid group(s) is (are) optionally modified by an amine or an alcohol respectively defined as NHR$^2$ and OR$^2$;
R$^3$ is H or a cationic entity preferably selected from the group comprising:
  metal cations advantageously selected from the subgroup comprising sodium, potassium, calcium and magnesium,
  organic cations advantageously selected from the subgroup comprising:
    cations based on amine,
    cations based on oligoamine,
    cations based on polyamine (polyethylenimine being particularly preferred), and
    cations based on one or more amino acids advantageously selected from the class comprising cations based on lysine or arginine, and
  cationic polyamino acids advantageously selected from the subgroup comprising polylysine and oligolysine;
C is a direct bond or a link group selected from an amino acid residue (preferably natural) and a hydroxy alcohol containing from 1 to 6 carbon atoms;
the groups D-GH independently of one another are each a radical in which:
  D is a link group —O—, —NH— or —N-alkyl- (C1 to C5), an amino acid residue (preferably natural), a diol, a diamine, an amino alcohol or a hydroxy acid containing from 1 to 6 carbon atoms, and
  GH is a hydrophobic group containing 8 to 30 carbon atoms:
    linear or branched C8 to C30 alkyls which can optionally contain at least one unit of unsaturation and/or at least one heteroatom (preferably O and/or N and/or S),
    C8 to C30 alkylaryls or arylalkyls which can optionally contain at least one unit of unsaturation and/or at least one heteroatom (preferably O and/or N and/or S), or
    C8 to C30 (poly)cyclics which can optionally contain at least one unit of unsaturation and/or at least one heteroatom (preferably O and/or N and/or S);
(n+q)/(q+p+o+n+m) is defined as the molar grafting rate of the hydrophobic groups GH and varies from 0.5 to 90 mol %;
q+p+o+n+m varies from 20 to 5000, preferably between 30 and 2000;
o+n+m (the skeleton) varies from 10 to 500, preferably between 30 and 300;
o/(o+n+m) is defined as the grafting rate of the branches and varies between 1 and 50 mol %;
the main chain Cp of these polyamino acids (I), (II) and (III) consists of the repeat units -[ ]$_o$-[ ]$_n$-[ ]$_m$- or -[ ]$_o$-[ ]$_m$- and their branches B consist of the repeat units -[ ]$_p$- or -[ ]$_p$-[ ]$_q$-;
and the hydrophobic groups GH and the branches B are in a random arrangement.

In a first embodiment of the invention, the main chain Cp and the branches B of the polyamino acids are alpha-L-glutamate or alpha-L-glutamic homopolymers.

In a second embodiment of the invention, the main chain Cp and the branches B of the polyamino acids are alpha-L-aspartate or alpha-L-aspartic homopolymers.

In a third embodiment of the invention, the main chain Cp and the branches B of the polyamino acids are alpha-L-aspartate/alpha-L-glutamate or alpha-L-aspartic/alpha-L-glutamic copolymers.

Advantageously, the distribution of the aspartic and/or glutamic units of the polyamino acid main chain is such that the resulting polymers are either random, or of the block type, or of the multiblock type.

It is furthermore preferable for the molar grafting rate of the polyamino acids according to the invention with hydrophobic units to be between 2 and 100%, preferably between 5 and 50%.

According to another definition, the polyamino acids according to the invention have a molecular weight of between 2000 and 800,000 g/mol, preferably of between 5000 and 300,000 g/mol.

In other variants, the polyamino acids according to the invention can carry at least one graft of the polyethylene glycol type bonded to a glutamate and/or aspartate unit.

Naturally, the invention also covers mixtures of polyamino acids as defined above.

For example, the hydrophobic branched polyamino acids according to the invention can comprise different types of main chains (or skeletons) which differ from one another in the number of "amino acid" units and/or the nature of said units.

The same applies to the branches B, which can be mutually identical or different in the number and/or nature of the "amino acid" units of which they are composed.

Remarkably, the polyamino acids of the invention can be used in several ways, depending on the nature of the hydrophobic groups and the degree of polymerization of the polyamino acid. The methods of forming a polymer for the encapsulation of an active principle in the various forms envisaged by the invention are known to those skilled in the art. For further details, reference may be made e.g. to the following few references of particular pertinence:

"Microspheres, Microcapsules and Liposomes; vol. 1. Preparation and chemical applications" Ed. R. Arshady, Citus Books 1999. ISBN: 0-9532187-1-6.

"Sustained-Release Injectable Products" Ed. J. Senior and M. Radomsky, Interpharm Press 2000. ISBN: 1-57491-101-5.

"Colloidal Drug Delivery Systems" Ed. J. Kreuter, Marcel Dekker, Inc. 1994. ISBN: 0-8247-9214-9.

"Handbook of Pharmaceutical Controlled Release Technology" Ed. D. L. Wise, Marcel Dekker, Inc. 2000. ISBN: 0-8247-0369-3.

These polyamino acids are also extremely valuable in that, depending on the length of the homopolymer (degree of polymerization) and the nature of the hydrophobic groups, they disperse in water at pH 7.4 (e.g. with a phosphate buffer) to give colloidal solutions or suspensions or structured or non-structured gels, depending on the homopolymer concentration. Furthermore, the polyamino acids (in particulate or non-particulate form) can encapsulate or easily associate with active principles such as proteins, peptides or small molecules. The preferred forming method is the one described in U.S. Pat. No. 6,630,171 in the name of the Applicant, which consists in dispersing the homopolymer in water and incubating the solution in the presence of an active principle (AP). This colloidal solution of vectorization particles consisting of the homopolyamino acids according to the invention can then be passed through a 0.2 µm filter and then injected directly into a patient.

When the hydrophilic/hydrophobic ratio decreases, the homopolymer can form microparticles capable of associating or encapsulating AP. In this context the microparticles can be formed by cosolubilizing the AP and the homopolymer in an appropriate organic solvent and then precipitating the mixture in water. The particles are subsequently recovered by filtration and can then be used for oral administration (in the form of gelatin capsules, in compacted and/or coated form, or else in the form of a dispersion in an oil) or for parenteral administration after redispersion in water.

In one variant the homopolymer can be solubilized in a biocompatible solvent such as N-methylpyrrolidone, or an appropriate oil such as Mygliol®, and then injected by the intramuscular or subcutaneous route or into a tumor. Diffusion of the solvent or oil leads to precipitation of the homopolymer at the injection site and thus forms a depot. These depots then ensure a controlled release by diffusion and/or by erosion and/or by hydrolytic or enzymatic degradation of the homo-polymer.

Independently of the fact that the microparticulate form of the polyamino acid according to the invention is preferred, the polymers of the invention, in neutral or ionized form, can more generally be used by themselves or in a liquid, solid or gel composition and in an aqueous or organic medium.

It should be understood that the polymer based on polyamino acids contains carboxyl groups which are either neutral (COOH form) or ionized ($COO^-$ anion), depending on the pH and the composition. For this reason the solubility in an aqueous phase is directly dependent on the proportion of free COOH in the polymer (not grafted with the hydrophobic unit) and the pH. In aqueous solution the countercation can be a metal cation such as sodium, calcium or magnesium, or an organic cation such as triethanolamine, tris(hydroxymethyl) aminomethane or a polyamine like polyethylenimine.

The polymers of the invention are obtained e.g. by methods known to those skilled in the art. First of all, it is pointed out that to obtain a polyamino acid of the alpha type, the most common technique is based on the polymerization of amino acid N-carboxy anhydrides (NCA), which is described e.g. in the article "Biopolymers" 1976, 15, 1869, and in the work by H. R. Kricheldorf entitled "Alpha-amino acid N-carboxy anhydrides and related heterocycles", Springer Verlag (1987). The NCA derivative is preferably NCA-Glu-O-Bz (Bz=benzyl) because the benzyl group can be selectively hydrolyzed without affecting other chemical groups of the homopolymers or the hydrophobic group.

A number of polymers that can be used according to the invention, e.g. of the poly(alpha-L-aspartic), poly(alpha-L-glutamic), poly(alpha-D-glutamic) and poly(gamma-L-glutamic) types of variable molecular weights, are commercially available. The polyaspartic polymer of the alpha-beta type is obtained by the condensation of aspartic acid (to give a polysuccinimide) followed by basic hydrolysis (cf. Tomida et al., Polymer 1997, 38, 4733-36).

The steps below illustrate the syntheses of the preferred polymers of the invention: polyglutamates of structures (I), (II) and (III). The mode of obtaining these polymers does not imply a limitation. Some synthesis schemes are given below by way of illustration. The polymerization and coupling reaction chemistry of the groups is conventional and well known to those skilled in the art (cf., for example, the above-cited patents or patent applications in the name of the Applicant).

A type (I) polymer can be synthesized according to the following steps:

1. synthesis of the skeleton: polyglutamic with an initiator/NCA monomer molar ratio of 1/(o+n+m). This polymerization is followed by hydrolysis, as described in patent application FR-A-2 801 226. The polymer is isolated in its polyacid form;
2. grafting of the hydrophobic grafts with groups GH onto the polymer using a molar ratio of n/(o+n+m) according to a method described in patent application WO-A-03/104303 in the name of the Applicant;
3. synthesis of the branches: idem above with an initiator/NCA monomer molar ratio of 1/(p+q), e.g. using an NCA of benzyl glutamate;
4. grafting of the branches onto the polymer using a molar ratio of o/(o+n+m);
5. hydrolysis of the benzyl groups to give the desired polymer.

A type (II) polymer can be synthesized analogously by first synthesizing the branched polymer without the hydrophobic grafts with groups GH, the grafting reaction of the hydrophobic grafts with groups GH being carried out last (step 2). The type (III) polymer can be synthesized by first grafting the hydrophobic grafts with groups GH onto the branches, the grafting of the branches being carried out in the last step.

These methods will be understood more clearly from the description of the Examples.

It must be observed that the degree of polymerization is defined by the molar ratio of the initiator to that of the polymer.

The coupling of the hydrophobic graft carrying GH with an acid group of the polymer is easily effected by reacting the polyamino acid in the presence of a carbodiimide as coupling agent, and optionally a catalyst such as 4-dimethylaminopyridine, in an appropriate solvent such as dimethylformamide (DMF), N-methyl-pyrrolidone (NMP) or dimethyl sulfoxide (DMSO). The carbodiimide is e.g. dicyclohexylcarbodiimide or diisopropylcarbodiimide. Other coupling reagents, such as chloroformates, can also be used (cf., for example, the work by Bodanszky entitled "Principles of Peptide Synthesis", Springer Verlag 1984, for examples of coupling agents). The grafting rate is controlled chemically by the stoichiometry of the constituents and reactants or by the reaction time. The hydrophobic grafts or the branches functionalized with an amino acid other than that of the polymer are obtained by conventional peptide coupling or by direct condensation under acid catalysis. These techniques are well known to those skilled in the art.

According to another of its features, the invention relates to a pharmaceutical, cosmetic, dietetic or phytosanitary composition comprising at least one polyamino acid as defined above and optionally at least one active principle, which can be a therapeutic, cosmetic, dietetic or phytosanitary active principle.

According to one valuable provision of the invention, the active principle is associated with the polyamino acid(s) by one or more bonds other than covalent chemical bonds.

The techniques of associating one or more AP with the grafted polyamino acids according to the invention are described in particular in U.S. Pat. No. 6,630,171. They consist in incorporating at least one active principle into the liquid medium containing vectorization particles (VP) in order to give a colloidal suspension of VP laden or associated with one or more active principles AP. This incorporation, which results in the AP being trapped by the VP, can be effected in the following manner:

introduction of AP into aqueous solution, followed by addition of the VP, either in the form of a colloidal suspension or in the form of isolated VP (lyophilizate or precipitate); or addition of AP, either in solution or in the pure or preformulated state, to a colloidal suspension of VP, optionally prepared for immediate use by the dispersion of dry VP in an appropriate solvent such as water.

Preferably, the active principle is a protein, a glycoprotein, a protein bonded to one or more polyalkylene glycol chains (preferably polyethylene glycol (PEG) chains: "PEGylated protein"), a polysaccharide, a liposaccharide, an oligo-nucleotide, a polynucleotide or a peptide.

In one variant the active principle is a "small" hydrophobic, hydrophilic or amphiphilic organic molecule.

As defined in the present disclosure, a "small" molecule is especially a small non-protein molecule.

The following may be mentioned as examples of AP that can be associated with the polyamino acids according to the invention, whether or not they are in the form of nanoparticles or microparticles:

proteins such as insulin, interferons, growth hormones, interleukins, erythropoietin or cytokines;

peptides such as leuprolide or cyclosporin;

small molecules such as those belonging to the anthracycline, taxoid or camptothecin family;

and mixtures thereof.

In one embodiment the composition of the invention is in the form of a gel, a solution, a suspension, an emulsion, micelles, nanoparticles, microparticles, an implant, a powder or a film.

In one of its particularly preferred forms, the composition, whether or not laden with active principle(s), is a stable colloidal suspension of nanoparticles and/or microparticles and/or micelles of polyamino acids in an aqueous phase.

In another embodiment the composition of the invention is in the form of a solution in a biocompatible solvent and can be injected by the subcutaneous or intramuscular route or into a tumor.

If the composition according to the invention is a pharmaceutical composition, it can be administered by the oral, parenteral, nasal, vaginal, ocular, subcutaneous, intravenous, intramuscular, intradermal, intraperitoneal, intracerebral or buccal route.

In another embodiment the composition can optionally contain an excipient to adjust the pH and/or the osmolarity, and/or to improve the stability (antioxidants) and/or as an antimicrobial. These excipients are well known to those skilled in the art (refer to the work entitled *Injectable Drug Development*, P. K. Gupta et al., Interpharm Press, Denver, Colo. 1999).

In another variant the composition according to the invention is formulated in such a way that it is capable of forming a depot at the injection site.

The invention further relates to compositions which comprise polyamino acids according to the invention and active principles and which can be used for the preparation of:

drugs, particularly for administration by the oral, nasal, vaginal, ocular, subcutaneous, intravenous, intramuscular, intradermal, intraperitoneal or intracerebral route, it being possible in particular for the active principles of these drugs to be proteins, glycoproteins, proteins bonded to one or more polyalkylene glycol chains {e.g. polyethylene glycol (PEG) chains, in which case the term "PEGylated" proteins is used}, peptides, polysaccharides, liposaccharides, oligonucleotides, polynucleotides and small hydrophobic, hydrophilic or amphiphilic organic molecules;

and/or nutriments;

and/or cosmetic or phytosanitary products.

According to yet another of its features, the invention relates to a process for the preparation of:

drugs, particularly for administration by the oral, nasal, vaginal, ocular, subcutaneous, intravenous, intramuscular, intradermal, intraperitoneal or intracerebral route, it being possible in particular for the active principles of these drugs to be proteins, glycoproteins, proteins bonded to one or more polyalkylene glycol chains {e.g. polyethylene glycol (PEG) chains, in which case the term "PEGylated" proteins is used}, peptides, polysaccharides, liposaccharides, oligonucleotides, polynucleotides and small hydrophobic, hydrophilic or amphiphilic organic molecules;

and/or nutriments;

and/or cosmetic or phytosanitary products, said process being characterized in that it consists essentially in using at least one homopolyamino acid as defined above and/or the composition also described above.

The invention further relates to a method of therapeutic treatment that consists essentially in administering the composition as described in the present disclosure by the oral, parenteral, nasal, vaginal, ocular, subcutaneous, intravenous, intramuscular, intradermal, intraperitoneal, intracerebral or buccal route.

In one particular variant of the invention, said method of therapeutic treatment consists essentially in introducing the composition as described above into solution in a biocompatible solvent and then injecting it by the subcutaneous or intramuscular route or into a tumor, preferably in such a way that it forms a depot at the injection site.

The invention will be better understood and its advantages and variants will become clearly apparent from the Examples below, which describe the synthesis of the branched homopolyamino acids, their conversion to an AP vectorization system (stable aqueous colloidal suspension) and the demonstration of the ability of such a system to associate with a protein to form pharmaceutical compositions.

EXAMPLES

Example 1

Synthesis of Polymer (1) of Type (I)

Indices and Groups
  m=108, n=8, o=4, p=15
  GH=D,L-alpha-tocopherol (T)
  A=—$CH_2$—$CH_2$—(glutamate); E=$NH_2$, E'=leucinamide; C, D direct bonds Step 1: Polymerization of the Branches and Coupling with pGluT Solution 1: In a 50 ml three-necked round-bottomed flask under a stream of nitrogen, 3.4 g of NCA GluOBn are dissolved in 9 ml of NMP at 25° C. 89 mg of leucinamide are added to the reaction medium. The polymerization is stopped at 80% conversion of the NCA by cooling the reaction medium to 0° C.

Solution 2: In parallel, 3.5 g of a polyglutamic acid with a degree of polymerization (DP) of 120, randomly grafted at a rate of 7 mol % with synthetic alpha-tocopherol (obtained by the procedure described in WO-A-03/104303), are solubilized in 44 ml of DMF by heating to 80° C. in a 100 ml three-necked round-bottomed flask. This solution is cooled to −15° C. and 128 ml of isobutyl chloroformate are added, followed by 109 ml of N-methylmorpholine. The reaction medium is stirred for 15 minutes, the temperature being allowed to rise to 0° C. The reaction medium is cooled again to −15° C. before solution 1 is added. The medium returns to room temperature and is then stirred for 2 hours at 40° C. The polymer is precipitated in acidified water (pH<2, 315 ml), filtered off, washed with acidified water (2×157 ml) and with iso ether (2×157 ml) and then dried in a vacuum oven at 40° C. to give 5.8 g of the intermediate branched polymer, i.e. a yield of 100%. The degree of polymerization of the branches, determined by $^1$H NMR in TFA-d, is 17.

Steps 2 and 3: Hydrolysis of the Benzyl Esters of the Branches and Neutralization 5.5 g of the above polymer are then dissolved at room temperature in 42 ml of TFA ($c_{poly}$=130 mg/ml). This solution is cooled to 0° C. and 6.8 ml of HBr (30% in acetic acid) are then added. The medium is then brought back to room temperature for 3 hours. The end of the reaction is monitored by $^1$H NMR in TFA-d and the reaction medium is poured into 300 ml of water containing ice. The precipitate is filtered off on a frit. The polymer is resolubilized in THF (42 ml) and then precipitated in diisopropyl ether, filtered off and washed with diisopropyl ether (3×85 ml). The product is finally dried in a vacuum oven at 40° C. to give 3.9 g of polymer (1) in its polyacid form (i.e. 82% yield).

The polymer is suspended in demineralized water and neutralized by adding 1 N NaOH solution. The neutralization has ended when all the polymer has been solubilized and the pH is around 7.4.

The percentage of tocopherol, determined by $^1$H NMR in TFA-d, is 4.6%. The Mn (determined by GPC in NMP) is 59.8 kg/mol in PMMA equivalents.

Example 2

Synthesis of Polymer (2) of Type (I)

Indices and Groups
  m=105, n=8, o=7, p=15
  GH=D,L-alpha-tocopherol (T)
  A=—$CH_2$—$CH_2$ (glutamate); E=$NH_2$, E'=glutamic acid diethyl ester; C, D=direct bonds Step 1: Polymerization of the Branches and Coupling with pGluT Solution 1: In a 50 ml three-necked round-bottomed flask under a stream of nitrogen, 5.9 g of NCA GluOBn are dissolved in 14 ml of NMP at 25° C. 243 mg of glutamic acid diethyl ester solubilized in 1 ml of NMP are added to the reaction medium. The polymerization is stopped at 80% conversion of the NCA by cooling the reaction medium to 0° C.

Solution 2: In parallel, 3.0 g of a polyglutamic acid with a degree of polymerization of 120, randomly grafted at a rate of 7 mol % with synthetic alpha-tocopherol (obtained by the procedure described in WO-A-03/104303), are solubilized in 44 ml of DMF by heating to 80° C. in a 100 ml three-necked round-bottomed flask. This solution is cooled to −15° C. and 219 ml of isobutyl chloroformate are added, followed by 186 ml of N-methylmorpholine. The reaction medium is stirred for 15 minutes, the temperature being allowed to rise to 0° C. The reaction medium is cooled again to −15° C. before solution 1 is added. The medium returns to room temperature and is then stirred for 2 hours at 40° C. The polymer is precipitated in acidified water (pH<2, 315 ml), filtered off on a frit, washed with acidified water (2×157 ml) and with iso ether (2×157 ml) and then dried in a vacuum oven at 40° C. to give 6.5 g of the intermediate polymer. The degree of polymerization of the branches, determined by $^1$H NMR in TFA-d, is 19.

Steps 2 and 3: Hydrolysis of the Benzyl Esters of the Branches and Neutralization 6.2 g of the above polymer are then dissolved at room temperature in 48 ml of TFA ($c_{poly}$=130 mg/ml). This solution is cooled to 0° C. and 11.5 ml of HBr (30% in acetic acid) are then added. The medium is then brought back to room temperature for 3 hours. The end of the reaction is monitored by $^1$H NMR in TFA-d and the reaction medium is poured into 335 ml of water containing ice. The precipitate is filtered off on a P4 frit. The polymer is resolubilized in THF (48 ml) and then precipitated in diisopropyl ether (480 ml), filtered off on a frit and washed with diisopropyl ether (2×48 ml). The product is finally dried in a vacuum oven at 40° C. to give 3.7 g of polymer (2) (i.e. 76% yield).

The polymer is suspended in demineralized water and neutralized by adding 1 N NaOH solution (so that the pH never exceeds a value of 8). The neutralization has ended when all the polymer has been solubilized and the pH is around 7.4.

The percentage of tocopherol, determined by $^1$H NMR in TFA-d, is 3.5%. The Mn (determined by GPC in NMP) is 42.4 kg/mol in PMMA equivalents.

Example 3

Synthesis of Polymer (3) of Type (I)

Indices and Groups
  m=105, n=8, o=7, p=8
  GH=D,L-alpha-tocopherol (T)
  A=—$CH_2$—$CH_2$ (glutamate); E=$NH_2$, E'=leucinamide; C, D=direct bonds 4.1 g of this polymer were synthesized by the process described in Example 1.

The degree of polymerization of the branches, determined by $^1$H NMR in TFA-d, is 10. The percentage of tocopherol, determined by $^1$H NMR in TFA-d, is 4.3%. The Mn (determined by GPC in NMP) is 66.3 kg/mol in PMMA equivalents.

Example 4

Synthesis of Polymer (4) of Type (I)

Indices and Groups
  m=25, n=7, o=3, p=15
  GH=D,L-alpha-tocopherol (T)
  A=—CH$_2$—CH$_2$ (glutamate); E=NH$_2$, E'=leucinamide; C, D=direct bonds 3.9 g of this polymer were synthesized by the process described in Example 2.

The degree of polymerization of the branches, determined by $^1$H NMR in TFA-d, is 18. The percentage of tocopherol, determined by $^1$H NMR in TFA-d, is 7.0%. The Mn (determined by GPC in NMP) is 24.1 kg/mol in PMMA equivalents.

Example 5

Synthesis of Polymer (5) of Type (II)

Indices and Groups
  m=103, n=5, o=12, p=30, q=1
  GH=D,L-alpha-tocopherol (T)
  A=—CH$_2$—CH$_2$ (glutamate); E=NH$_2$, E'=leucinamide; C, D=direct bonds Step 1: Polymerization of the Branches, Coupling with pGluOH and Hydrolysis of the Esters of the Branches Solution 1: In a 250 ml three-necked round-bottomed flask under a stream of nitrogen, 20.0 g of NCA GluOMe are dissolved in 86 ml of NMP at 40° C. 345 mg of leucinamide dissolved in 4 ml of NMP are added to the reaction medium. The polymerization is stopped at 80% conversion of the NCA by cooling the reaction medium to 0° C.

Solution 2: In parallel, 3.3 g of a polyglutamic acid of DP 120 are solubilized in 52 ml of DMF by heating to 80° C. in a 500 ml three-necked round-bottomed flask. This solution is cooled to 0° C. and 502 ml of isobutyl chloroformate are added, followed by 426 ml of N-methylmorpholine. The reaction medium is stirred at 0° C. during the polymerization of solution 1. 71 ml of N-methylmorpholine are added before solution 1. The medium returns to room temperature and is stirred for 4.5 hours at this temperature. The temperature of the medium is then raised to 80° C. A solution of NMP/35% HCl (14.5 ml/28.5 ml) is added dropwise at this temperature and the pressure in the flask is lowered to 600 mbar. After 5 days of hydrolysis, the polymer is precipitated in acidified water (pH<2, 710 ml), centrifuged off and washed with acidified water (200 ml) and then with water (2×200 ml). The polymer is filtered off on a frit and then dried in a vacuum oven at 40° C. to give 12.3 g of the intermediate polymer (i.e. 90% yield). The degree of polymerization of the branches, determined by $^1$H NMR in TFA-d, is 50.

Steps 2 and 3: Grafting of the Tocopherol and Neutralization 5.0 g of the above polymer are dissolved at 80° C. in 100 ml of DMF ($c_{poly}$=50 mg/ml). 47 mg of DMAP solubilized in 0.6 ml of DMF are added to this solution. The medium is maintained at 80° C. for 18 hours. The temperature is then lowered to 15° C. and the following are added in order: a solution of tocopherol (834 mg in 2.6 ml of DMF), a solution of DMAP (50 mg in 0.6 ml of DMF) and DIPC (546 mg). The reaction medium is stirred at this temperature for 3.5 hours. It is blocked with 35% HCl (4.0 ml) and the polymer is then precipitated in a two-phase medium of acidified water (400 ml, 60 g of NaCl, pH<2) and diisopropyl ether (80 ml). The product is washed three times with a two-phase mixture of acidified water and diisopropyl ether (3×300/80 ml) and then twice with diisopropyl ether (2×300 ml). The product is finally dried in a vacuum oven at 40° C. to give 5.1 g of polymer (5) (i.e. 87% yield).

The polymer is suspended in demineralized water and neutralized by adding 1 N NaOH solution. The neutralization has ended when all the polymer has been solubilized and the pH is around 7.4.

The percentage of tocopherol, determined by $^1$H NMR in TFA-d, is 4.5%. The Mn (determined by GPC in NMP at 70° C.) is 248.6 kg/mol in PMMA equivalents.

Example 6

Syntheses of Linear-Type Compounds C1, C2, C3 and C4

These compounds are obtained by the method described in patent application WO-A-03/104303.

The characteristics of these polymers are given in the Table below.

Example 7

Studies of the Solubility and Viscosity Properties

To compare the properties and demonstrate the invention, the viscosity of the polymer is measured as a function of concentration at pH 7.4 and at an osmolality of 300 mOsmol. The limiting aggregation concentration C$\eta$ (g/l), i.e. the concentration beyond which the viscosity increases very rapidly, is then measured. The results and the characteristics of the polymers of the invention and the comparative compounds of the prior art are collated in Table 1 below.

TABLE 1

| Example | Type | Total DP | mol % of GH | C$\eta$ (g/l) |
|---|---|---|---|---|
| 1 | branched, type I | 180 | 4.6 | 35 |
| 2 | branched, type I | 230 | 3.5 | 70 |
| 3 | branched, type I | 180 | 4.3 | 40 |
| 4 | branched, type I | 85 | 7.0 | 100 |
| 5 | branched, type II | 480 | 4.5 | 20 |
| C1 | linear | 120 | 7.3 | 20 |
| C2 | linear | 120 | 4.0 | 28 |
| C3 | linear | 220 | 5.0 | 25 |
| C4 | linear | 500 | 4.1 | 10 |

C$\eta$ is the limiting aggregation concentration, i.e. the concentration beyond which the viscosity increases very rapidly.
The total DP corresponds to the degree of polymerization of the branched or linear polymer.

Comparison of the viscosities, illustrated by the C$\eta$ values, shows that it is much easier to obtain a concentrated solution with the polymers of the invention. In particular, comparison of the polymers having a skeleton of analogous size and an equivalent grafting rate, on the one hand (1), (2) and (3) versus C1 and C2 and on the other hand (5) versus C4, clearly demonstrates this difference. This property therefore makes it possible to prepare formulations with high polymer concentrations, thereby making it possible to increase the polymer/active principle ratio, while at the same time ensuring a good injectability.

Example 8

Study of Association with Insulin

An aqueous solution of pH 7.4 containing 10 mg of polymer per milliliter and 200 IU of insulin (7.4 mg) is prepared.

The solutions are incubated for two hours at room temperature and the free insulin is separated from the associated insulin by ultrafiltration (cut-off at 100 kDa, 15 minutes under 10,000 G at 18° C.). The free insulin recovered from the filtrate is then measured quantitatively by HPLC (high performance liquid chromatography) and the amount of associated insulin is deduced. The results are given in Table 2 below.

TABLE 2

| Polymer | % association |
|---|---|
| 1 | 96 |
| 2 | 90 |
| 5 | 99 |

The results demonstrate that the polymers of the invention are capable of associating insulin strongly to give colloidal suspensions with a size in excess of 100 kDa, and the insulin association rates are very high. The association capacity of these polymers makes them suitable for use as vectorization agents.

The invention claimed is:

1. A polyamino acid comprising an amino acid unit selected from aspartic units, glutamic units or a mixture of aspartic units and glutamic units, wherein at least one of said aspartic units or glutamic units carries one or more mutually identical or different hydrophobic groups (GH), wherein said GH is coupled with an acid group of said polyamino acid, wherein said polyamino acid comprises at least one type of polyamino acid main chain Cp comprising aspartic units or glutamic units and having one or more mutually identical or different polyamino acid branches B comprising aspartic units or glutamic units, and wherein said GH is selected from the group consisting of:
linear or branched C8 to C30 alkyl groups, linear or branched C8 to C30 alkyl groups comprising at least one unit of unsaturation or at least one heteroatom, C8 to C30 alkylaryl or arylalkyl groups, C8 to C30 alkylaryl or arylalkyl groups further comprising at least one unit of unsaturation or at least one heteroatom, C8 to C30 (poly)cyclic groups, and C8 to C30 (poly)cyclic groups comprising at least one unit of unsaturation or at least one heteroatom.

2. The polyamino acid of claim 1, wherein the hydrophobic group (GH) is derived from a group selected from the group consisting of: octanol, dodecanol, tetradecanol, hexadecanol, octadecanol, oleyl alcohol, tocopherol, cholesterol and lithocholic acid.

3. The polyamino acid of claim 1, wherein said aspartic units and/or glutamic units are selected from alpha-L-glutamate units, alpha-L-glutamic units, alpha-L-aspartate units, and alpha-L-aspartic units.

4. The polyamino acid of claim 1, wherein said polyamino acid has one of general formulae (I), (II) and (III) below:

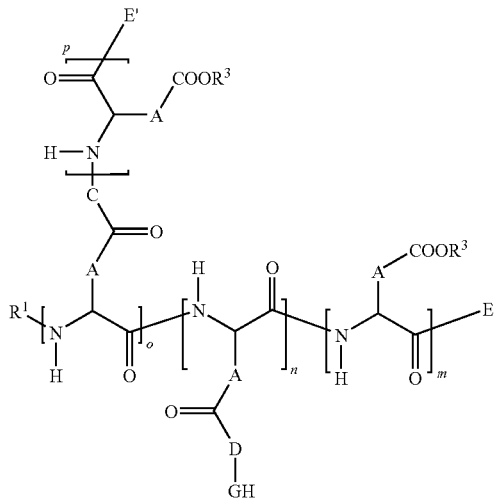

(I)

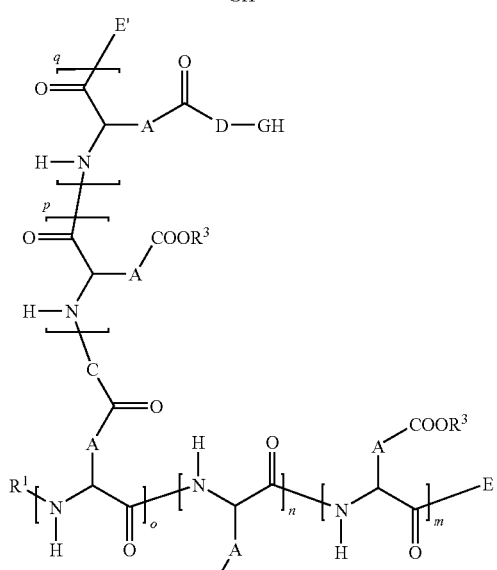

(II)

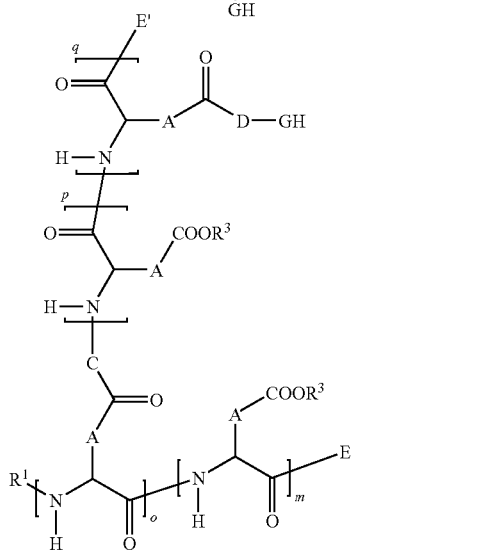

(III)

in which:

i) A independently is —CH$_2$— or —CH$_2$—CH$_2$—;

ii) R$^1$ is H, a linear C2 to C10 or branched C3 to C10 acyl group, or pyroglutamate;

iii) E, E' independently are:
   a) OR$^3$ wherein R$^3$ is H or a cationic entity selected from: metal cations, organic cations, and cationic polyamino acids;
   b) a group NHR$^2$ wherein R$^2$ is H, a linear C2 to C10 or branched C3 to C10 alkyl, or a benzyl;
   or
   c) a terminal amino acid unit which is bonded by the nitrogen and whose acid group(s) is (are) optionally modified by an amine or an alcohol respectively defined as NHR$^2$ and OR$^2$;

iv) R$^3$ is H or a cationic entity selected from: metal cations, organic cations, and cationic polyamino acids;

v) C is a direct bond or a link group selected from an amino acid residue and a hydroxy alcohol containing from 1 to 6 carbon atoms;

vi) the groups D-GH independently of one another are each a radical wherein:

D is selected from the group consisting of: a link group —O—, a link group —NH—, a link group —N—alkyl-(C1 to C5), an amino acid residue, a diol, a diamine, an amino alcohol and a hydroxy acid containing from 1 to 6 carbon atoms, and GH is a hydrophobic group containing 8 to 30 carbon atoms selected from the group consisting of: linear or branched C8 to C30 alkyls, linear or branched C8 to C30 alkyls which contain at least one unit of unsaturation and/or at least one heteroatom, C8 to C30 alkylaryls or arylalkyls, C8 to C30 alkylaryls or arylalkyls which contain at least one unit of unsaturation and/or at least one heteroatom, C8 to C30 (poly)cyclics, and C8 to C30 (poly)cyclics which contain at least one unit of unsaturation and/or at least one heteroatom;

vii) (n+q)/(q+p+o+n+m) is defined as the molar grafting rate of the hydrophobic groups (GH) and varies from 0.5 to 90 mol %;

viii) q+p+o+n+m varies from 20 to 5000;

ix) o+n+m (the skeleton) varies from 10 to 500;

x) o/(o+n+m) is defined as the grafting rate of the branches and varies between 1 and 50 mol %;

xi) the main chain Cp of these polyamino acids (I), (II) and (III) consists of the repeat units -[ ]$_o$-[ ]$_n$-[ ]$_m$- or -[ ]$_o$-[ ]$_m$- and their branches B consist of the repeat units -[ ]$_p$- or -[ ]$_p$-[ ]$_q$-;

and xii) the hydrophobic groups (GH) and the branches B are in a random arrangement.

5. The polyamino acid of claim 1, wherein the molecular weight of said polyamino acid is between 2000 and 800,000 g/mol.

6. A pharmaceutical, cosmetic, dietetic or phytosanitary composition comprising at least one polyamino acid according to claim 1.

7. The composition of claim 6, wherein said composition comprises at least one active principle associated with the polyamino acid(s) by one or more bonds other than covalent chemical bonds.

8. The composition of claim 7, wherein the active principle is selected from the group consisting of: a protein, a glycoprotein, a protein bonded to one or more polyalkylene glycol chains, a polysaccharide, a liposaccharide, an oligonucleotide, a poly-nucleotide and a peptide.

9. The composition of claim 7, wherein the active principle is a small hydrophobic, hydrophilic or amphiphilic organic molecule.

10. The composition of claim 6, wherein said composition can be administered by oral, parenteral, nasal, vaginal, ocular, subcutaneous, intravenous, intramuscular, intradermal, intraperitoneal, intracerebral or buccal routes.

11. The composition of claim 6, wherein said composition is in the form of a gel, a solution, an emulsion, micelles, nanoparticles, microparticles, a powder or a film.

12. The composition of claim 6, wherein said composition is a colloidal suspension of nanoparticles and/or microparticles and/or micelles of polyamino acids in an aqueous phase.

13. The composition of claim 6, wherein said composition is in the form of a solution in a biocompatible solvent that can be injected by a subcutaneous or intramuscular route or into a tumor.

14. The composition of claim 13, wherein said composition is capable of forming a depot at the injection site.

15. A process for obtaining the polyamino acids according to claim 4, said process comprising the steps of:
   1) synthesizing the polyamino acid skeleton by polymerizing polyglutamic N-carboxy anhydride (NCA), polyaspartic N-carboxy anhydride (NCA) or a mixture thereof with an initiator/NCA monomer molar ratio of 1/(o+n+m);
   2) grafting hydrophobic grafts with groups (GH) onto the polyamino acid skeleton using a molar ratio of n/(o+n+m);
   3) synthesizing branch(es) B by polymerizing polyglutamic N-carboxy anhydride (NCA), polyaspartic N-carboxy anhydride (NCA) or a mixture thereof with an initiator/NCA monomer molar ratio of 1/(p+q);
   4) grafting branch(es) B onto the polyamino acid skeleton using a molar ratio of o/(o+n+m); and
   5) hydrolyzing the product obtained at step 4) to give the desired polyamino acid.

* * * * *